United States Patent [19]

Anderson

[11] Patent Number: 4,701,892
[45] Date of Patent: Oct. 20, 1987

[54] DOWNHOLE CASING INSPECTION SYSTEM

[75] Inventor: Leo J. Anderson, Lake Jackson, Tex.

[73] Assignee: Sonar & Wells Testing Services, Inc., Houston, Tex.

[21] Appl. No.: 909,852

[22] Filed: Sep. 22, 1986

Related U.S. Application Data

[63] Continuation-in-part of Ser. No. 583,555, Feb. 27, 1984, abandoned.

[30] Foreign Application Priority Data

Feb. 19, 1986 [CA] Canada .................................. 502228

[51] Int. Cl.$^4$ ........................... G01V 1/40; G01V 1/00
[52] U.S. Cl. ..................................... 367/35; 367/153; 367/912; 181/103; 181/105
[58] Field of Search ............... 181/102, 103, 104, 105, 181/106, 111, 112, 107, 108; 367/25, 27, 33, 35, 86, 53, 155, 911, 912

[56] References Cited

U.S. PATENT DOCUMENTS

| | | | |
|---|---|---|---|
| 3,859,620 | 1/1975 | Percy ................................. | 181/112 |
| 4,380,808 | 4/1983 | Hill et al. ............................ | 367/153 |
| 4,468,665 | 8/1984 | Thawley et al. ..................... | 317/76 |
| 4,601,024 | 7/1986 | Broding ............................... | 367/86 |
| 4,607,352 | 8/1986 | Seeman et al. ....................... | 367/35 |

Primary Examiner—Deborah L. Kyle
Assistant Examiner—Brian S. Steinberger
Attorney, Agent, or Firm—Glwynn R. Baker

[57] ABSTRACT

A 60 to 100% coverage of downhole casing condition is obtainable by the improved system comprising, a sufficient number of piezoelectric transducers ¼ inch in diameter about a probe head, preferably, 40 or more and usually 60-120 piezoelectric transducers located in a housing coupled to an electronic package also in a suitable downhole housing. The system reports all exceptional data and certain selected regular or non-exceptional data, displaying it topside and establishing a permanent record using existing wire line facilities.

5 Claims, 3 Drawing Figures

DOWNHOLE CASING INSPECTION SYSTEM

CROSS REFERENCE TO RELATED APPLICATIONS

This application is a continuation-in-part of my earlier filed appliction Ser. No. 583,555, entitled downhole casing inspection system, filed Feb. 27, 1984, now abandoned.

BRIEF DESCRIPTION OF THE INVENTION

The present invention comprises a downhole casing inspection system composed of
a probe,
an electronics package,
a communications link,
a topside controller, and
auxiliaries.

The probe preferably contains sufficient piezoelectric transducers of ¼ to ½" diameter indented within and through a housing in a pattern such as to scan about 60% of the interior wall surface of the tube when pulled at a rate of about 20 feet per minute. The housing is of a dimension and structural composition to slide into a well casing with from ¼ inch minimum to about 3 inch maximum clearance and to withstand downhole pressures. Preferably the probe should be of a size to have an annulus between it and the interior well casing of ½ to 1 inch. The tranducers are of a number and a pattern to provide at the 1 inch annular spacing 60-100% coverage of the circumferential area of the incremental length being examined. The probe also may incorporate a centering device, e.g. a leaf spring system, integral with or attached to the probe body as a downhole extension (Stinger) of the probe body.

The electronics package is of a similar housing structure with a centering device embodied thereon. The electronics package is preferably of a size to fit the probe and contains preferably a pulsar and amplifier for each transducer and associated elements to fire each transducer in a non interfering sequence one with the other at the selected rate of travel of the probe and package up the casing to cover 60-100% of the incremental length being examined. The electronics package also contains an analog to digital signal converter (A/D), a clock, a computing section, a comparison section, a memory, and a transmitting section.

The communications link is at present a 7 wire insulated cable containing a multi-wire draw cable associated therewith. While a 7 wire cable is conventional and readily available at most field sites it is to be understood that cables of a greater number of wires would be desired and advantageous in order to transmit more data more rapidly.

The top side controller and auxiliaries are a central processing unit, CRT and printers programmed to translate the signal impulses received from the communications link into readable data and images.

DETAILED DESCRIPTION OF THE INVENTION

In accordance with the present invention a downhole casing inspection system is comprised of
(a) a probe
(b) an electronic package
(c) a communications link
(d) a topside controller
(e) auxiliaries—CRT display, Printer, tape storage, etc.

A stylized diagram of these elements is shown in line drawing FIG. 1.

The Probe

Figure 1:
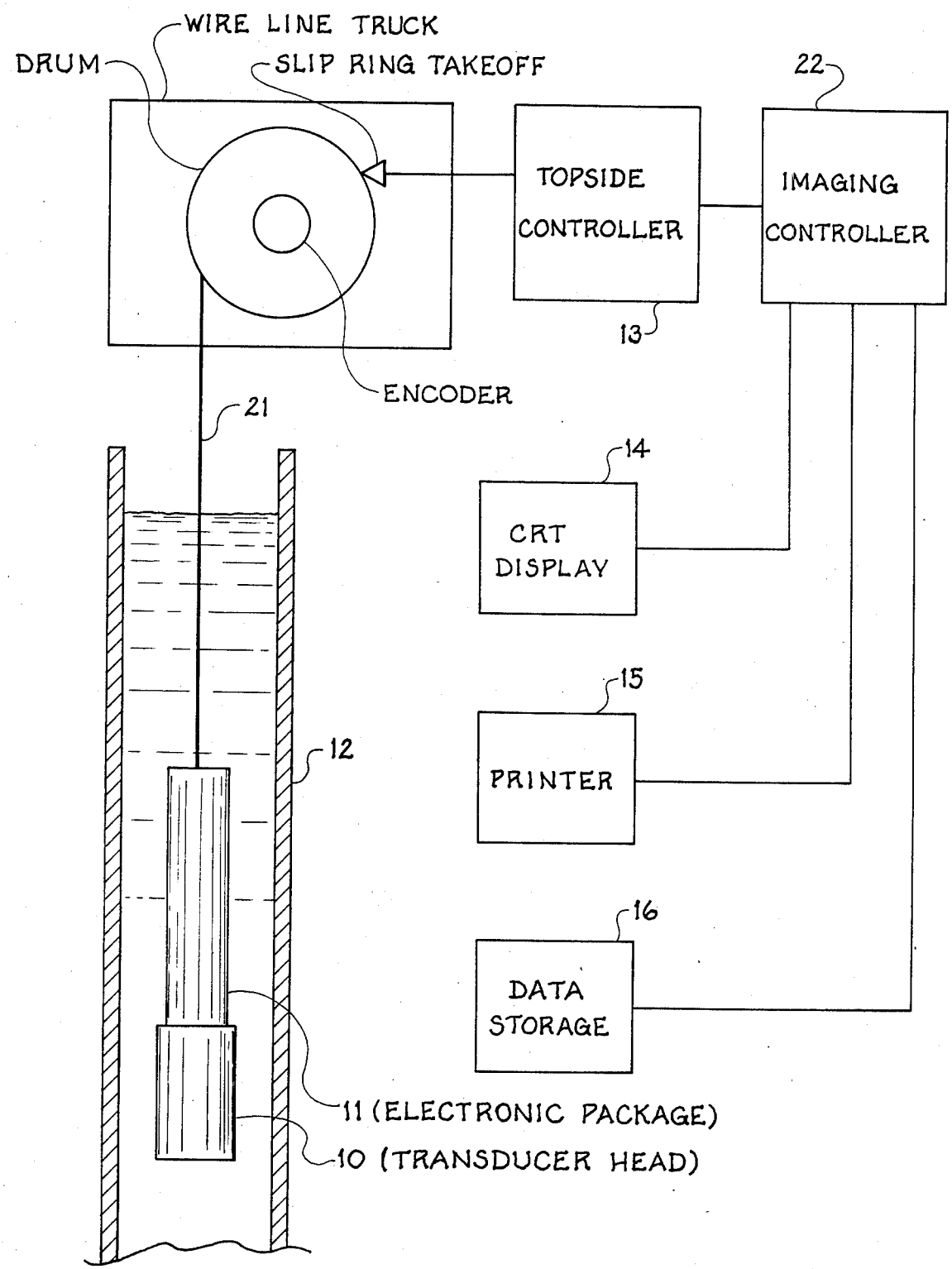

The probe of the present invention is a cylindrical member having positioned within its confines but extending through the surface a number of conventional piezoelectric transducers (sound) wave generators. The number of transducers is sufficient based on the total diameter of the waves of the several transducers in the pattern, to impinge on at least 60% of the circumferential inner surface of a longitudinal segment or increment of a casing being examined when the complete pattern is fired when pulled at a rate of about 20 feet per minute. In practice it has been found desirable to employ at least 40 ¼ inch transducers to scan 60% of a four inch tube and preferably at least 60 ¼ inch transducers in a 3 inch diameter probe aligned in 6 staggered rows since the probe will scan 100 percent of a 4 inch casing at a 20 foot per minute pull rate. While the 40 transducer head will scan 60% of a four inch tube at a 20 foot per minute pull, it will scan even less of 5 or 6 inch tube unless the pull rate is markedly reduced. In the interest of providing a single head to cover 4 to 7½ inch tubes from 100% to 60%, respectively, at a reasonable rate of pull, the 3 inch diameter head with 60 transduces staggered in six rows is preferred. Likewise, to scan 100 percent of a 9⅞ inch casing 120 transducers are necessary again aligned in staggered pattern of at 6 rows. Casings between 4 inch and 7+ are scanned with the sized probe having 60¼ inch transducers. The 120¼ inch transducer probe is used to scan casings of from 9⅝" to 16" in order to impinge on at least 60% of the inner circumferential surface of the casing when pulled at the reasonably fast rate of 20 feet per minute. It is to be understood that less than 100% coverage is obtained as the casing diameter increases without a comparable increase in the number of transducers and/or transducers having larger diameter wave patterns.

In addition to the working transducers there is provided a calibrating transducer.

It is preferable that the probe be of a size to have no greater than about 1 inch annular space between the probe surface and the inner casing wall surface. Thus, it is preferred that a probe be made for each 2 inch change in diameter of casing, i.e. a probe for 4-6, 7-9, 10-12 etc. However, it is to be understood that an annular space of two inches is operable but may not be as sensitive due to the greater distance the wave must travel and the fanning out of the wave pattern.

The transducer head or probe may have associated with it (integral with but down hole, e.g. a stinger) a centering device such as a leaf spring.

The Electronic Package

The electronic package of the present invention consists of various computer elements which include a clock, a switch, a multiplexer, an analog to digital converter, a transmitter, and associated storage capacity. These components are programmed to initiate the sequential firing of multiple transducers receive the echo signal from the interior wall and the exterior wall including imperfections in surface characteristic, convert the echo which is an analog signal to a digital signal and make comparisons with a standard relative to surface defects, eccentricity of the casing, joints, etc. These comparisons are signaled to the surface preferably only when exceptional data is obtained. The presently concerned program for transmitting data to the surface is based on the fact that the communications link is a 7 wire cable thus limiting the number of transmissions to the surface when the reasonable draw rate of 20 feet per minute is employed. Thus, it is contemplated that when defects are found close together the data will be greater than the transmission rate capability and thus a memory of such exceptional data must be a component part programmed to transmit and "catch-up" during the period when the data generated is normal i.e., no exceptional data is evidenced.

The electronics package preferably has a centering device associated with it as well as a power supply from topside.

The Communications Link

The communications link is the industry standard 7 conductor armored wire line.

While more wires would be advantageous the cost for providing on site an insulated 9, 15 or 21 conductor wire line of at least 12000 feet or more would out-weigh the advantages obtained by having greater instantaneous data transmission capability.

The Topside Controller

The topside controller is a computer processing unit (CPU) programmed to receive the data being transmitted, convert it for recording and imagining both instantaneously and in permanent printed form both pictorially as well as numerically.

The Auxiliaries

The auxiliaries are components compatible with the topside controller such as CRT, printers, and the like which generate the physical imagery of the data.

The downhole elements of the system are designed and built to withstand the downhole pressures (usually in excess of 5000 psi) and are constructed from materials which will withstand the numerous corrosive components found in downhole casings of brine wells, oil and gas wells and the like.

Measurements

Figure 2:
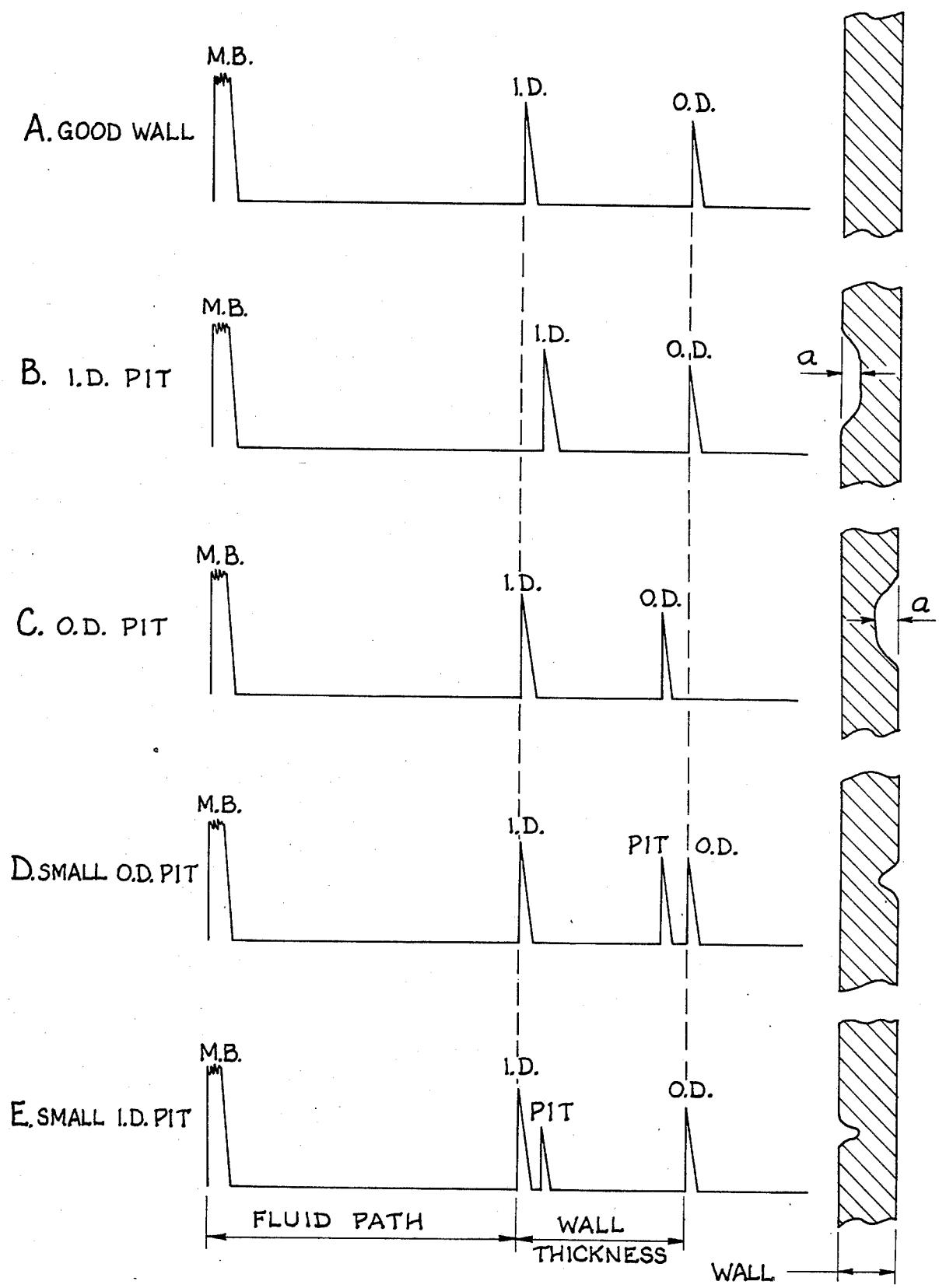
FIG. 2 illustrates the signal response (time of flight) as seen on a CRT display for various conditions of an increment of the casing being examined.
Figure 3:
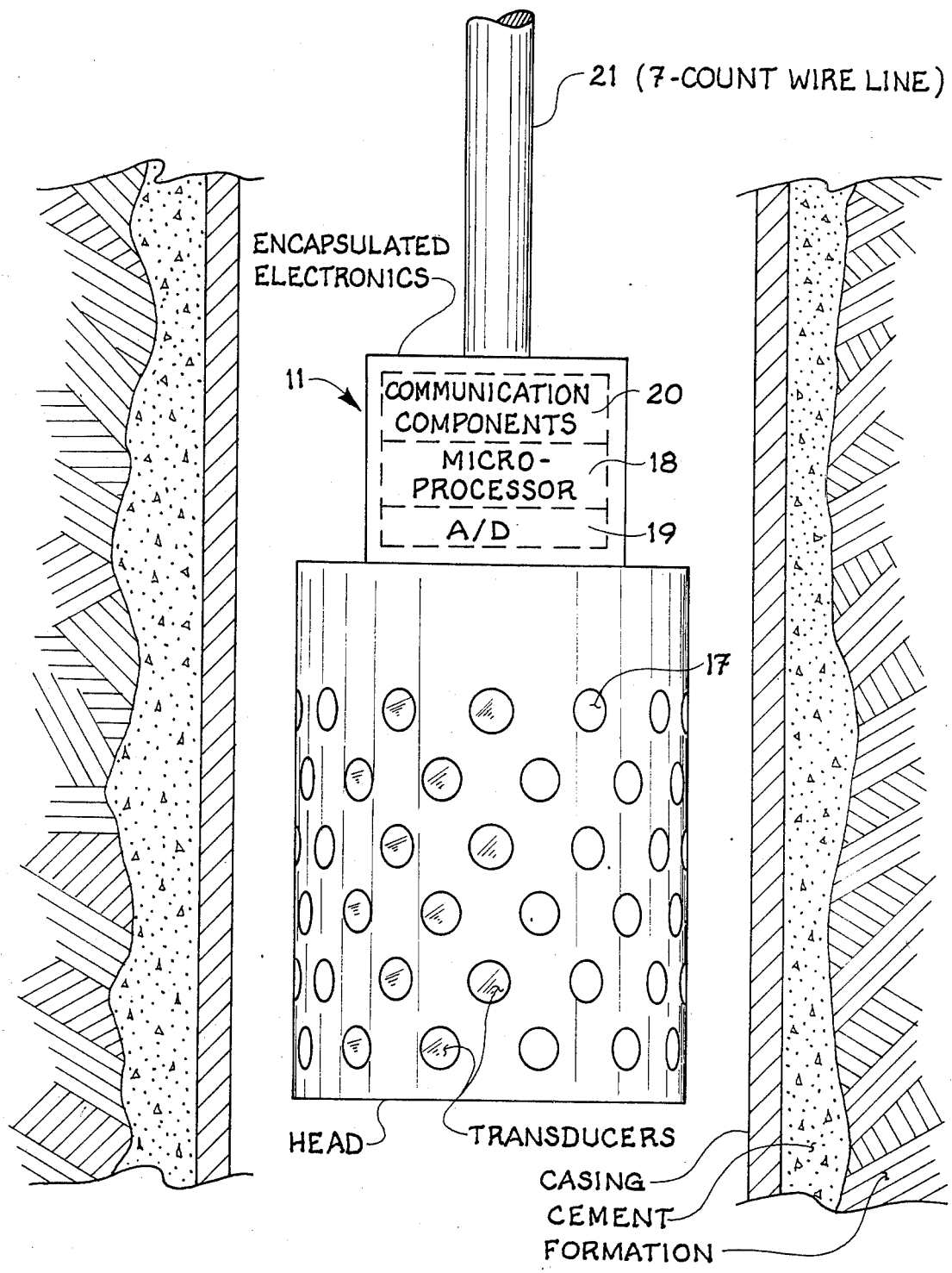
FIG. 3 illustrates the preferred transducer spacing, A/D, the electronics package and the wire-line.

The basic method of measurement and inspection is illustrated in FIG. 2. The detection of a corrosion pit on the inside diameter of the well casing is accomplished by measuring the increased time-of-flight for an acoustic pulse through a fluid path that results from a corrosion pit on the inside diameter (FIG. 2b). Vis-a-vis the time of flight to the unpitted wall surface. Note that the OD reflection as well as the ID reflection may be shifted out in time.

A pit on the outside diameter results in a decreased time-of-flight in the casing wall only—the ID reflection remains in the same place (FIG. 2c). Depending on the size of the pit, the OD reflection may actually be comprised of two echoes as in FIG. 2d. This poses no problem, however, since the echo from the bottom of the pit occurs first, and we can readily time to it if it has sufficient amplitude.

The case shown in FIG. 2e does pose a problem, however. Here, a small pit reflection occurs after the ID reflection. A portion of the transducer beam is reflected by the ID surface and the bottom of the pit also reflects part of the beam. This problem was solved by selecting the transducer geometry so that the required standard pit causes the ID reflection to disappear as in FIG. 2b. Small pits whose geometry or size does not cause the ID reflection to shift in time (as in FIG. 2b) will be ignored.

The basic measuring scheme is:
a. Measure the time-of-flight of the acoustic pulse from the Main Bang to the first echo (ID).
b. Measure the time-of-flight in the casing wall from the ID (first echo) to the OD (second echo).

From the basic measurements the desired casing parameters will be derived:
a. Remaining Wall Thickness
b. Eccentricity of the Casing
c. Location of the Corrosion (ID or OD)

Exceptional data (data transmitted to the Topside Controller) is defined as: (a) Remaining wall below acceptable thickness or (b) Casing Eccentricity greater than acceptable. A thin wall condition will activate the process of determining the location (ID or OD) of the corrosion. Periodic Eccentricity measurements (a sample every foot or so) is made and sent to the surface even though they are not exceptional. The detection of exceptional Eccentricity will increase the sample rate.

Temperature Compensation

Since the temperature and the composition of the coupling fluid can vary widely during the course of a well test, it was necessary to provide a method of compensating for these variations. To accomplish this an additional measurement channel was added. This channel ultrasonically measures the velocity of propagation of ultrasound in the coupling fluid, and this measurement will be used to correct preferably in the electronic package the fluid path measurement.

Topside Controller

The task of the Topside Controller is basically that of a communication link with and a power source for the Down Hole Probe. It also is required to assemble and perform some preliminary analysis of the incoming data. The functions of the Topside Controller are:
1. Receive the data transmitted by the Down Hole Probe.
2. Transmit control and pull rate data to the Down Hole Probe.
3. Keep track of the depth of the Down Hole Probe.
4. Provides the Power Interface to the Down Hole Probe.
5. Does final data processing and transfers the data to the imaging controller, printers, etc.

Image Controller

The Image Controller provides more detailed data analysis and displays the data in a form the operator can interpret. The Image Controller:
1. Receives data from the Topside Controller.
2. Stores the exceptional data on a magnetic mass storage media.
3. Displays the data momentarily so the operator can view it.
4. Provides a condensed report of the Exceptional data.

If all the data from a 6000 foot well were to be stored, about 70 M Bytes of data storage would be required. Assuming that the desired pull rate of 20 feet/minute is maintained, less than ⅓ of the total available data (about 23 M Bytes) can be transmitted to the surface for storage, however.

The data is displayed (while data is being taken) momentarily (a few seconds) showing each short section of the casing with the exceptional data highlighted. The image is formed on a standard CRT and employs standard graphic display boards.

The condensed report of the Exceptional data summarizes the test.

I claim:

1. A downhole casing interior and exterior wall inspection tool comprising
   a. a multiple element transducer head package containing at least a multiplicity of ¼ inch diameter transducers which transmit a signal and receive returns of said signal from the interior and exterior surfaces of said casing the number of said transducers being at least a sufficient to scan at least 60% of the inner wall surface of said casing, each transducer spaced apart from the other in a manner to transmit a signal unidirectionally towards the casing wall closest to said transducer and further said transducers being spaced in a pattern such that when a multiplicity of said transducers which are not adjacent to one another are fired the return from those fired will not interfere with the return from a near by fired transducer and said package containing a calibration transducer,
   b. an electronic package associated with such transducer head package containing an component to convert the return signals from each transducer to a digitalized signal communicatable to a contained programmed micro-processor of said package, said microprocessor component programmed to report return signals which are different in time of return from a standard expected when the casing is in good condition and further preprogrammed to report a preprogrammed number of signals commensurate with that expected when the casing is in good condition but not all such signals as received from the transducer head package, through a communication component to a surface located CPU,
   c. the communications component operatively associated with the electronic package enables communications of the output of the micro-processor, via wire-line, to the CPU at the surface,
   d. the CPU at the surface programmed to visualize and report the signals which are received as significant from the expected norm as well as the preprogrammed number of expected signal returns,
   said transducer head package having each transducer spaced circumferentially and longitudinally in a staggered pattern of about 6 rows such that the signals generated from the transducers will scan from about 60 to about 100% of the interior of the casing when substantially all transducers in said package have been activated in a sequential pattern such that no two adjacent transducers are activated in sequence thus avoiding interference with an adjacent fired transducer's return at the speed of pull of the package past a longitudinal segment to be examined.

2. The system of claim 1 wherein at least 40¼ inch transducers are provided.

3. The system of claim 1 wherein 120¼ inch transducers are provided.

4. A downhole casing interior and exterior wall inspection tool comprising
   a. a multiple element transducer head package containing at least a multiplicity of at least 40¼ inch diameter transducers which transmit a signal and receive returns of said signal from the interior and exterior surface of said casing to scan at least 60% of the inner wall surface of said casing, each transducer spaced apart from the other in a manner to transmit a signal unidirectionally towards the casing wall closest to said transducer and further said transducers being spaced in a pattern such that when a multiplicity of said transducers which are not adjacent to one another are fired the return from those fired will not interfere with the return from a near by fired transducer and said package containing a calibration transducer,
   b. an electronic package associated with such transducer head package containing an component to convert the return signals from each transducer to a digitalized signal communicatable to a contained programmed micro-processor of said package, said microprocessor component programmed to report return signals which are different in time of return from a standard expected when the casing is in good condition and further preprogrammed to report a preprogrammed number of signals commensurate with that expected when the casing is ingood condition but not all such signals as received from the transducer head package, through a communication component to a surface located CPU,
   c. the communications component operatively associated with the electronic package enables communications of the output of the micro-processor, via wire-line, to the CPU at the surface,
   d. the CPU at the surface programmed to visualize and report the signals which are received as significant from the expected norm as well as the preprogrammed number of expected signal returns,
   said transducer head package having each transducer spaced circumferentially and longitudinally in a staggered pattern of about 6 rows such that the signals generated from the transducers will scan from about 60 to about 100% of the interior of the casing when substantially all transducers in said package have been activated in a sequential pattern such that no two adjacent transducers are activated in sequence thus avoiding interference with an adjacent fired transducer's return at the speed of pull of the package past a longitudinal segment to be examined.

5. A downhole casing interior and exterior wall inspection tool comprising
   a. a multiple element transducer head package containing at least a multiplicity of at least 60¼ inch diameter transducers which transmit a signal and receive returns of said signal from the interior and exterior surfaces of said casing the number of said transducers being at least a sufficient to scan at least 60% of the inner wall surface of said casing, each transducer spaced apart from the other in a manner to transmit a signal unidirectionally towards the casing wall closest to said transducer and further said transducers being spaced in a pattern such that when a multiplicity of said transducers which are not adjacent to one another are fired the return from those fired will not interfere with the return from a near by fired transducer and said package containing a calibration transducer, b. an electronic package associated with such transducer head package containing an component to convert the return signals from each transducer to a digitalizd signal communicatable to a contained programmed micro-processor of said package said microprocessor component programmed to report return signals which are different in time of return from a standard expected when the casing is in good condition and further preprogrammed to report a preprogrammed number of signals commensurate with that expected when the casing is ingood condition but not all such signals as received from the transducer head package, through a communication component to a surface located CPU, c. the communications component operatively associated with the electronic package enables communications of the output of the micro-processor, via wire-line, to the CPU at the surface, d. the CPU at the surface programmed to visualize and report the signals which are received as significant from the expected norm as well as the preprogrammed number of expected signal returns, said transducer head package having each transducer spaced circumferentially and longitudinally in a staggered pattern of about 6 rows such that the signals generated from the transducers will scan from about 60 to about 100% of the interior of the casing when substantially all transducers in said package have been activated in a sequential pattern such that not two adjacent transducers are activated in sequence thus avoiding interference with an adjacent fired transducer's return at the speed of pull of the package past a longitudinal segment to be examined.

* * * * *